United States Patent
Gono (10) Patent No.: US 8,500,632 B2
(45) Date of Patent: Aug. 6, 2013

(54) ENDOSCOPE AND ENDOSCOPE APPARATUS

(75) Inventor: Kazuhiro Gono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1250 days.

(21) Appl. No.: 11/917,286

(22) PCT Filed: Jun. 22, 2006

(86) PCT No.: PCT/JP2006/312528
§ 371 (c)(1),
(2), (4) Date: Dec. 12, 2007

(87) PCT Pub. No.: WO2007/010709
PCT Pub. Date: Jan. 25, 2007

(65) Prior Publication Data
US 2009/0082625 A1 Mar. 26, 2009

(30) Foreign Application Priority Data
Jul. 15, 2005 (JP) .................................. 2005-207509

(51) Int. Cl.
*A61B 1/06* (2006.01)
*A61B 6/00* (2006.01)
*A61B 1/04* (2006.01)
*G01J 3/30* (2006.01)
*G01J 3/42* (2006.01)

(52) U.S. Cl.
USPC ........... 600/181; 600/160; 600/476; 600/109; 356/317; 356/320

(58) Field of Classification Search
USPC ................. 600/181, 475, 309, 109, 178, 162, 600/160, 310, 410, 476, 478, 317, 473, 321; 348/273, 277, 68, 241, 46, 70, 76, 65, 71, 348/243, 45; 356/72, 301, 425, 317, 51, 320, 356/407
See application file for complete search history.

(56) References Cited

U.S. PATENT DOCUMENTS

| | | | | |
|---|---|---|---|---|
| 4,878,113 A | * | 10/1989 | Nakamura | 348/71 |
| 4,884,133 A | | 11/1989 | Kanno et al. | |
| 4,885,634 A | * | 12/1989 | Yabe | 348/71 |
| 4,961,110 A | * | 10/1990 | Nakamura | 348/70 |
| 5,001,556 A | * | 3/1991 | Nakamura et al. | 348/70 |

(Continued)

FOREIGN PATENT DOCUMENTS

| | | |
|---|---|---|
| CN | 1398108 A | 2/2003 |
| CN | 2616170 Y | 5/2004 |

(Continued)

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An endoscope includes an elongated insertion portion having a distal end portion provided with an illumination window and an observation window. A single solid-state image sensing device whose image pickup face is provided at an image forming position of an objective optical system mounted on the observation window. In the vicinity of the image pickup face of the solid-state image sensing device, a filter portion that has a first filter having a wideband wavelength transmission characteristic in a visible band and a second filter having a narrowband wavelength transmission characteristic in the visible band two-dimensionally arranged is disposed.

11 Claims, 6 Drawing Sheets

U.S. PATENT DOCUMENTS

| | | | |
|---|---|---|---|
| 5,255,087 A * | 10/1993 | Nakamura et al. | 348/71 |
| 5,293,872 A * | 3/1994 | Alfano et al. | 600/475 |
| 5,604,530 A * | 2/1997 | Saito et al. | 348/70 |
| 5,827,190 A * | 10/1998 | Palcic et al. | 600/476 |
| 6,070,096 A * | 5/2000 | Hayashi | 600/477 |
| 6,293,911 B1 * | 9/2001 | Imaizumi et al. | 600/160 |
| 6,516,217 B1 * | 2/2003 | Tsujita | 600/477 |
| 6,800,057 B2 * | 10/2004 | Tsujita et al. | 600/160 |
| 2001/0049473 A1 * | 12/2001 | Hayashi | 600/317 |
| 2002/0007122 A1 | 1/2002 | Kaufman et al. | |
| 2002/0013512 A1 * | 1/2002 | Sendai et al. | 600/160 |
| 2002/0014595 A1 * | 2/2002 | Sendai et al. | 250/458.1 |
| 2002/0161283 A1 * | 10/2002 | Sendai | 600/160 |
| 2002/0168096 A1 * | 11/2002 | Hakamata et al. | 382/132 |
| 2003/0001104 A1 * | 1/2003 | Sendai et al. | 250/458.1 |
| 2003/0001951 A1 * | 1/2003 | Tsujita et al. | 348/65 |
| 2003/0007087 A1 * | 1/2003 | Hakamata et al. | 348/370 |
| 2003/0013937 A1 * | 1/2003 | Tsujita et al. | 600/109 |
| 2003/0016295 A1 | 1/2003 | Nakakuki | |
| 2003/0197781 A1 * | 10/2003 | Sugimoto et al. | 348/72 |
| 2003/0216626 A1 * | 11/2003 | Tsujita et al. | 600/321 |
| 2004/0082833 A1 * | 4/2004 | Adler et al. | 600/109 |
| 2004/0148141 A1 * | 7/2004 | Tsujita et al. | 702/190 |
| 2004/0186351 A1 * | 9/2004 | Imaizumi et al. | 600/160 |
| 2005/0029437 A1 * | 2/2005 | Hasegawa et al. | 250/226 |
| 2005/0096505 A1 | 5/2005 | Imaizumi et al. | |
| 2005/0154277 A1 * | 7/2005 | Tang et al. | 600/407 |
| 2005/0212933 A1 * | 9/2005 | Miyanohara | 348/272 |
| 2005/0234302 A1 * | 10/2005 | MacKinnon et al. | 600/181 |
| 2005/0288553 A1 * | 12/2005 | Sugimoto | 600/118 |
| 2005/0288556 A1 * | 12/2005 | Sugimoto | 600/160 |
| 2006/0058684 A1 * | 3/2006 | Sendai | 600/476 |
| 2006/0149133 A1 * | 7/2006 | Sugimoto et al. | 600/160 |
| 2006/0173240 A1 * | 8/2006 | Fukuyama et al. | 600/118 |
| 2006/0232668 A1 * | 10/2006 | Horn et al. | 348/71 |
| 2010/0224796 A1 * | 9/2010 | Mertz et al. | 250/459.1 |

FOREIGN PATENT DOCUMENTS

| | | |
|---|---|---|
| EP | 1 067 376 A2 | 1/2001 |
| EP | 1 527 729 | 5/2005 |
| JP | 60-53922 | 3/1985 |
| JP | 04-357926 | 12/1992 |
| JP | 06-315477 | 11/1994 |
| JP | 2001-178674 | 7/2001 |
| JP | 2002-095635 | 4/2002 |
| JP | 2003-093336 | 4/2003 |
| JP | 2004-000477 | 1/2004 |
| JP | 2005-131130 | 5/2005 |

* cited by examiner

ENDOSCOPE AND ENDOSCOPE APPARATUS

TECHNICAL FIELD

The present invention relates to an endoscope and an endoscope apparatus for performing endoscopy by emitting illumination light of a visible band into a body cavity or the like.

BACKGROUND ART

In conventional endoscope apparatuses, in order to generate a normal image, image pickup is performed by emitting white light using solid-state image sensing devices that have color filters having wideband color transmission characteristics, or by emitting surface-sequential wideband illumination light of R, G, B or the like using monochrome solid-state image sensing devices.

On the other hand, in body tissues, light absorption characteristics and spectral characteristics vary depending on wavelengths of emitted light. For example, in Japanese Unexamined Patent Application Publication No. 2002-95635, as a first known art, there is disclosed an endoscope apparatus for narrowband observation that emits narrowband RGB surface-sequential light in a visible band on a body tissue, and obtains tissue information at a desired depth of the body tissue.

Moreover, in Japanese Unexamined Patent Application Publication No. 2003-93336, as a second known art, there is disclosed an electronic endoscope that performs signal processing with respect to an image signal for generating a normal image that is obtained by illumination light of a visible band to generate a discrete spectral image (or, narrowband image) and obtain narrowband image information with respect to a body tissue.

In the second known art, there is disclosed an electronic endoscope provided with R, G, B filters for separating colors in a wide band in a visible band so that normal images are generated.

In the first known art, an optical narrowband bandpass filter is employed. However, in the apparatus according to the second known art, without using the optical narrowband bandpass filter, a narrowband image signal is generated by performing signal processing.

Moreover, as a third known art, in Japanese Unexamined Patent Application Publication No. 4-357926, there is disclosed an endoscope apparatus that can obtain a normal image in a visible band and an infrared or ultraviolet image other than the visible band.

In the third known art, there is disclosed the electric endoscope that has color filters of cyan (Cy), G, yellow (Ye) that separate colors in a wide band in the visible band, and the color filters are set to have characteristics to further transmit infrared light.

Moreover, as a forth known art, in FIG. 14 in an endoscope apparatus in Japanese Unexamined Patent Application Publication No. 6-315477, there is disclosed an electronic endoscope that forms images on a CCD which splits incident light using a beam splitter and is provided with a color filter for normal images, and on a CCD which is provided with narrowband filters for special light (more specifically, for acquisition of blood information).

In the first known art, it is necessary to change the illumination light depending on whether a normal image or a narrowband image is to be obtained.

On the other hand, in the second known art, it is not necessary to change the illumination light, and the illumination light of the visible band is constantly emitted.

Based on the signal captured under the illumination light, estimation processing of the narrowband image signal is electrically performed. Accordingly, the processing is apt to be effected by a reflection characteristic or the like of the observation subject. Accordingly, as compared with the first known art, it is difficult to generate narrowband image signals excellent in precision.

That is, in the second known art, it is difficult to generate reliable narrowband images.

In the third known art, it is possible to obtain the infrared or ultraviolet image, however, it is not possible to generate narrowband image signals in illumination conditions to obtain normal images.

In the forth known art, it is possible to obtain normal images and narrowband images under illumination of white light. However, two CCDs, for the normal images and for the narrowband images, are disposed in a distal end portion of an insertion portion of the electronic endoscope. Accordingly, the insertion portion is wide, and it is disadvantageous.

The present invention has been made in view of the above, and an object of the present invention is to provide an endoscope and an endoscope apparatus capable of narrowing a diameter of an insertion portion and capable of generating a normal image and a narrowband image using illumination of illumination light in a visible band.

DISCLOSURE OF INVENTION

Means for Solving the Problem

The present invention provides an endoscope that includes an elongated insertion portion having a distal end portion provided with an illumination window and an observation window; an objective optical system mounted on the observation window; a single solid-state image sensing device whose image pickup face is disposed at an image forming position of the objective optical system; and a filter portion that is disposed in the vicinity of the image pickup face of the solid-state image sensing device, and that has a first filter having a wideband wavelength transmission characteristic in a visible band and a second filter having a narrowband wavelength transmission characteristic in the visible band two-dimensionally arranged.

The above configuration enables to generate the normal image using the wideband first filter and the narrowband image using the narrowband second filter under the illumination of the visible band illumination light, and also enables to narrow the diameter of the insertion portion using the single-solid-state image sensing device.

BRIEF DESCRIPTION OF THE DRAWINGS

FIG. 5 is a view illustrating spectral characteristics of a narrowband λ1 filter or the like.

BEST MODE FOR CARRYING OUT THE INVENTION

Hereinafter, embodiments of the present invention will be described with reference to the drawings.
(First Embodiment)

A first embodiment of the present invention will be described with reference to FIGS. 1 to 6B.

In the present embodiment, a single solid-state image sensing device is provided with filters for normal image generation, the filters have wideband wavelength transmission characteristics in a visible band, and a narrowband filter for narrowband image generation, the filter has a narrowband wavelength transmission characteristic, and the filters are arranged in a filter array to form a unit pixel for generation of both images. The configuration realizes to narrow a diameter of an insertion portion of an endoscope.

Further, according to the configuration, even if image pickup is performed under white light for normal image generation or illumination light having a spectral characteristic similar to the white light, high precision narrowband images can be obtained in real time as a matter of course the normal images.

Moreover, according to the present embodiment, an endoscope apparatus suitable for observation or diagnosis of vascular networks in a surface layer of biological mucous membrane in a body cavity is provided with a configuration capable of simultaneously displaying a normal image and a narrowband image without switching of illumination light.

Figure 1:
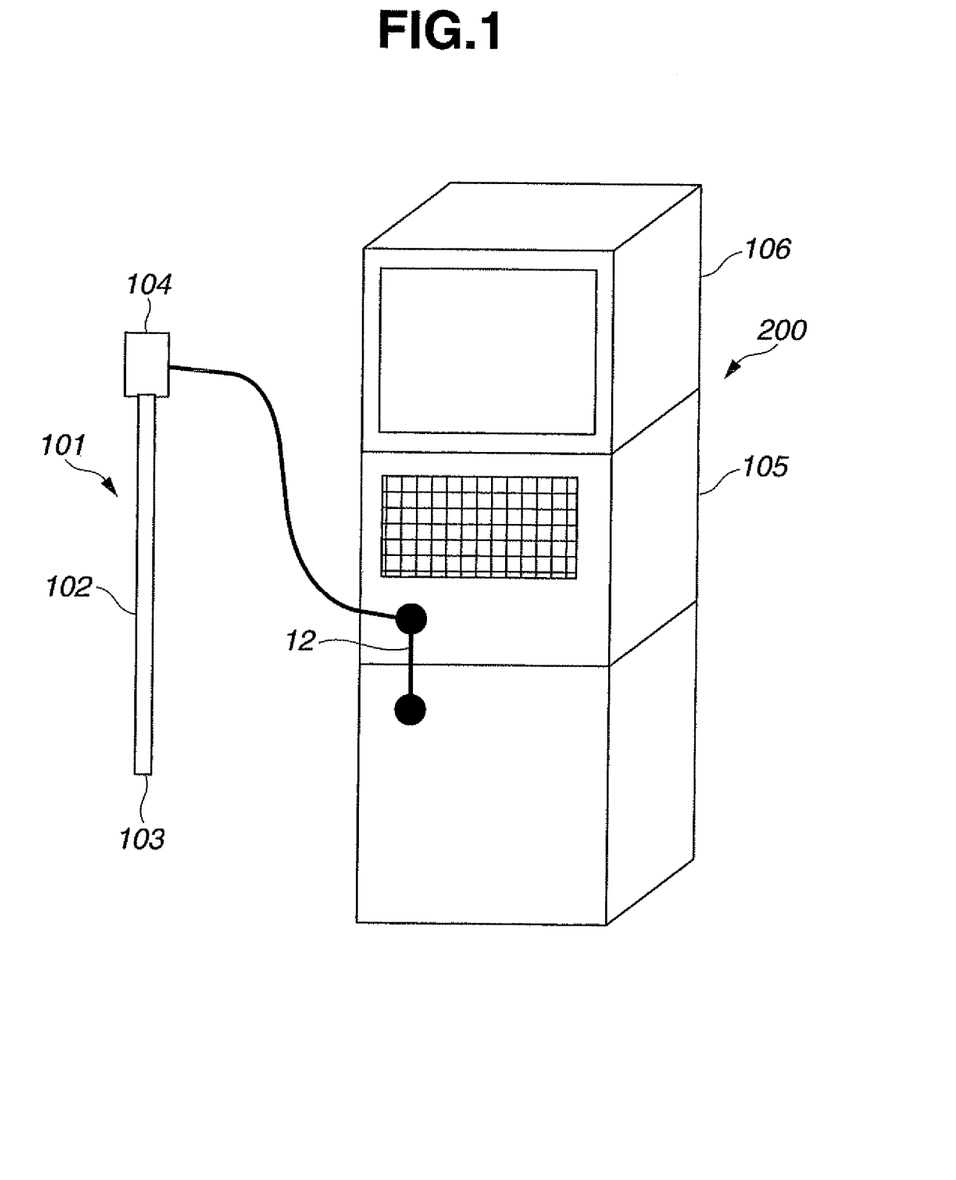
FIG. 1 is an outline view of an electronic endoscope apparatus according to a first embodiment of the present invention.

An electronic endoscope apparatus 200 according to the first embodiment of the present invention shown in FIG. 1 includes an electronic endoscope (briefly referred to as scope) 101 that has an illumination window and an observation window (image pickup window), an endoscope apparatus body 105 to which the scope 101 is detachably connected, and performs signal processing with respect to image pickup means, and a display monitor 106 that displays and outputs a biological signal outputted from the endoscope apparatus body 105.

Figure 2:
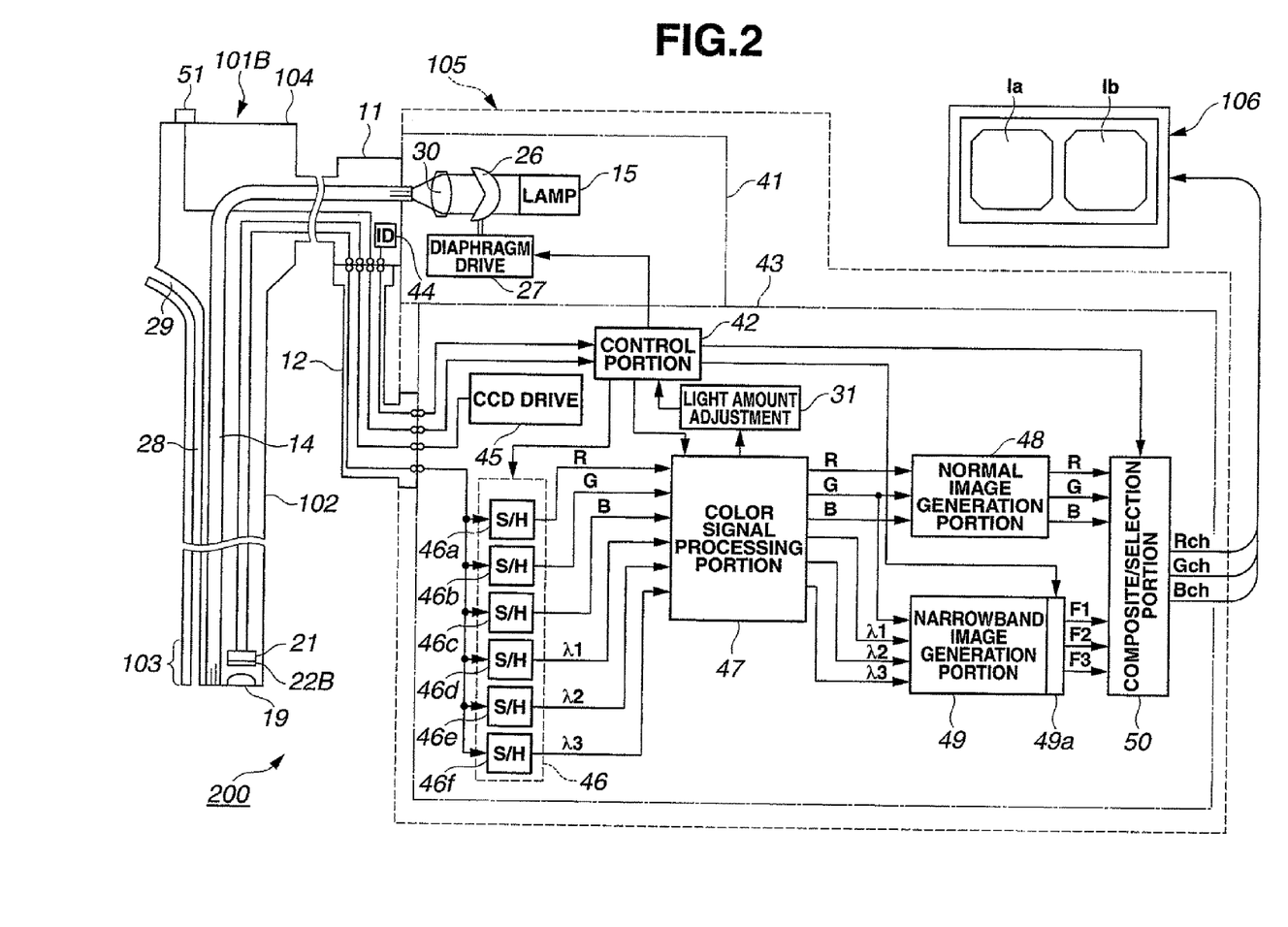
FIG. 2 is a block diagram illustrating a configuration of the electronic endoscope apparatus according to the first embodiment of the present invention.

To the endoscope apparatus body 105, one of the scope 101 shown in FIG. 1 and a scope 101B shown in FIG. 2 is selectively connected.

The scope 101 includes, as main components, an elongated insertion portion 102 that is inserted into a body cavity of a patient or the like, a distal end portion 103 that is provided at a distal end of the insertion portion 102, and an operation portion 104 that is provided at a proximal end side opposite to the distal end side of the insertion portion 102, and has an angle operation portion (not shown) for instructing bending operation or the like at the side of the distal end portion 103.

The electronic endoscope apparatus 200 according to the present embodiment employs the endoscope apparatus body 105 that corresponds to the scope 101B that is provided with a solid-state image sensing device whose color filter portion is different from that of the scope 101 in the configuration.

On an image of the inside of a subject obtained by the scope 101, predetermined signal processing is performed in the endoscope apparatus body 105, and on the display monitor 106, the processed image is displayed.

As shown in FIG. 2, the endoscope apparatus body 105 includes a light source portion 41 that generates illumination light in a visible band and a body processing device 43 that has a built-in control portion 42 for performing control and functions as an endoscope signal processing device.

In the present embodiment, the description is made on the premise that the endoscope apparatus body 105 has the light source portion 41 and the body processing device 43 for performing image processing or the like in the inside. However, these components may be configured as independent units.

To the light source portion 41, the scope 101 or the scope 101B is detachably connected via a connector 11, and the light source portion 41 is connected to the control portion 42 of the body processing device 43. The light source portion 41, based on a signal transmitted from the control portion 42, supplies illumination light of an appropriate amount to the scope 101 or the scope 101B.

The light source portion 41 includes, a lamp 15 such as a xenon lamp as a light source for generating illumination light (specifically, white light) in a visible band, a diaphragm 26 for adjusting an amount of light, and a diaphragm drive portion 27 for driving the diaphragm 26 and vary its opening amount.

The light emitted from the lamp 15 passes through the diaphragm 26 and is condensed by a condenser 30 disposed on the optical path. The condensed light enters into an incident end of the light guide 14 as illumination light, the light guide 14 function as illumination light transmission means provided in the scopes 101 and 101B that are detachably connected to the light source portion 41 via the connector 11.

The illumination light entered into the incident end of the light guide 14 is transmitted to a distal end face of the light guide 14 that is inserted through the inside of the insertion portion 102. The distal end face of the light guide 14 is mounted on an illumination window that is provided in the distal end portion 103 of the insertion portion 102. Illumination light outputted from the illumination window illuminates surfaces of living tissues or the like in the body cavity.

Moreover, an observation window into which observation light enters is provided adjacent to the illumination window in the distal end portion 103. An objective optical system 19 is mounted on the observation window. At a position where an image is formed in the objective optical system 19, an image pickup face of a charge coupled device (hereinafter, briefly referred to as CCD) 21 that functions as a solid-state image sensing device is disposed, and the formed optical image is photoelectrically converted.

To the diaphragm drive portion 27, based on the signal captured by the CCD 21, a light amount control signal generated by a light amount control circuit 31 is supplied via the control portion 42. The diaphragm drive portion 27 controls an opening amount of the diaphragm 26 to approximate to a target light amount.

By the control of the opening amount, the illumination light amount to be supplied to the light guide 14 is automatically controlled to be a target light amount corresponding to appropriate luminance.

The CCD 21 employed in the present embodiment is a single-CCD type (CCD employed for simultaneous electronic endoscopes).

On the image pickup face of the CCD 21, a color filter portion 22 or a color filter portion 22B that optically separates colors is provided. In the color filter portion 22 or the color filter portion 22B, together with color filters that have wideband transmission characteristics, a narrowband filter that has a narrowband transmission characteristic is two-dimensionally arranged. That is one of characteristics of the color filter portions.

That is, in the present embodiment, on the single-CCD 21, the color filter portion 22 or the color filter portion 22B including the wideband color filters (more specifically, three color filters for performing normal color image pickup) and the narrowband filter is provided.

According to the configuration, the scope 101 or the scope 101B can realize the narrow diameter distal end portion 103 of the insertion portion 102, and enables to simultaneously generate a normal image and a narrowband image. Moreover, with the configuration of the scope 101 or the scope 101B provided with the single-CCD 21, it is enough to provide one CCD drive circuit in the body processing device 43 for performing signal processing.

Figure 3A:
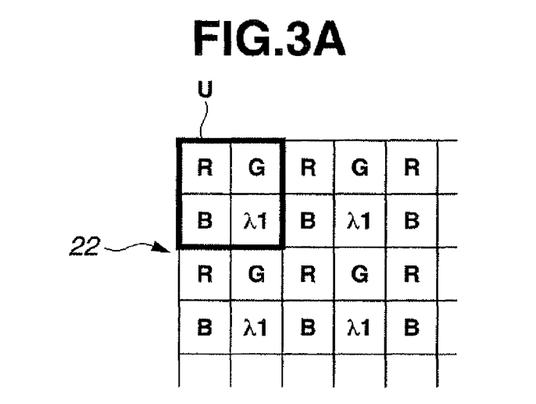
FIG. 3A is a view illustrating a filter array configuration of a color filter portion in one scope.

In the scope 101, on the image pickup face of the CCD 21, as shown in FIG. 3A, R, G, B filters that function as the color filters for separating colors in a wide band, and a narrowband filter of $\lambda 1$ are provided.

The four filters of R, G, B filters, and $\lambda 1$ filter form a unit filter array U that corresponds to a unit pixel for generating a normal image (visible band image) and a narrowband image. The color filter portion 22 is formed by two-dimensionally arranging the filters in a period of the unit filter array U.

Figure 4:
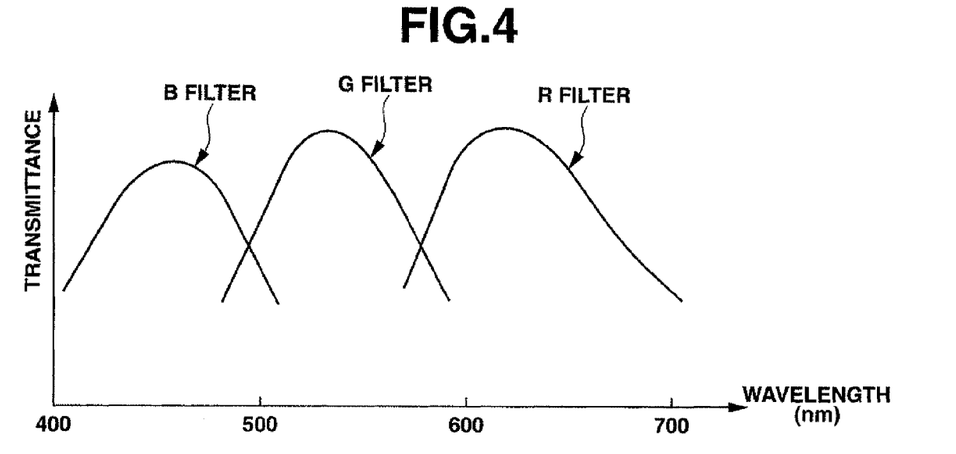
FIG. 4 is a view illustrating spectral characteristics of wideband RGB filters.

The R, G, B filters have transmission characteristics as shown in FIG. 4 to transmit in wavelengths of R, G, B in a wide band respectively to cover the visible band.

Figure 5:
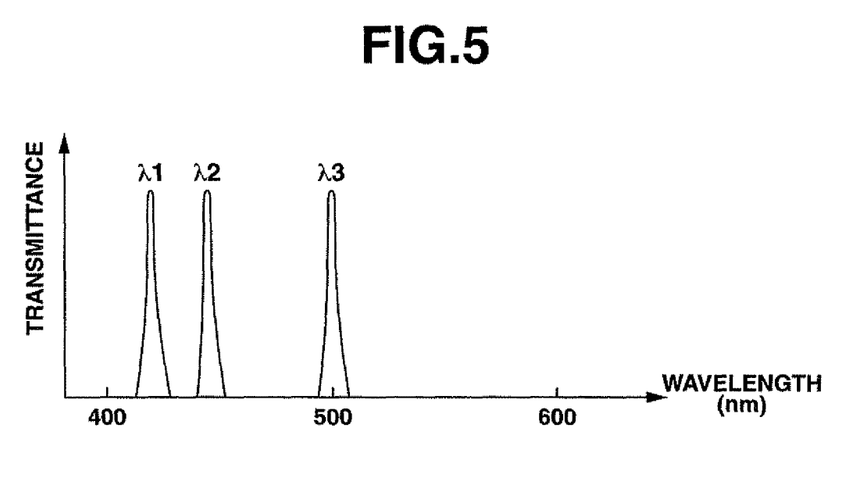

On the other hand, a spectral characteristic of the $\lambda 1$ filter as the narrowband filter, that is, a transmission factor characteristic with respect to a wavelength, is set to be a narrowband characteristic, for example, as shown in FIG. 5, to a side of a blue short wavelength, more specifically, to a narrow band of a central wavelength of 420 nm, and a half bandwidth of about 30 nm.

According to the configuration of the color filter portion 22, it is possible to simultaneously form a normal observation image using the R, G, B filters, and a narrowband image using the G filter and the $\lambda 1$ filter by performing color adjustment as described below.

Figure 3B:
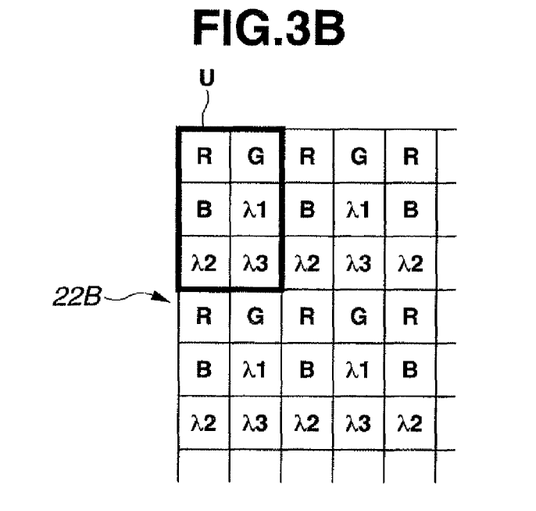
FIG. 3B is a view illustrating a filter array configuration of a color filter portion in the other scope.

On the other hand, the scope 101B includes the CCD 21 that incorporates the color filter portion 22B as shown in FIG. 3B. The color filter portion 22B includes, in addition to the R, G, B, filters and the $\lambda 1$ filter, a $\lambda 2$ filter and a $\lambda 3$ filter as two narrowband filters. In the configuration, the six filters constitute the unit filter array U. The color filter portion 22B is formed by vertically and horizontally, and two-dimensionally arranging the filters in a period of the unit filter array U. Transmission characteristics of the $\lambda 2$ filter and the $\lambda 3$ filter in the configuration are shown in FIG. 5 that illustrates the transmission characteristic of the $\lambda 1$ filter. The $\lambda 2$ filter and the $\lambda 3$ filter are set to have narrowband characteristics, for example, as shown in FIG. 5, to a narrow band characteristic of a central wavelength of 445 nm, and 500 nm, and a half bandwidth of about 30 nm respectively.

The endoscope apparatus body 105 according to the present embodiment can be applied to both of the scope 101 shown in FIG. 1, the scope 101 has the color filter portion 22 shown in FIG. 3A, and the scope 101B that has the color filter portion 22B shown in FIG. 3B. It is noted that the scope 101 and the scope 101B differ from each other, for example, only in the configurations of the color filter portions 22 and 22B.

The scope 101 and the scope 101B respectively include, for example, ID portions 44 that generate identification information (ID) in the connector 11. The control portion 42 in the endoscope apparatus body 105 reads the ID from a scope connected to the endoscope apparatus body 105 to determine the type of the scope, and perform corresponding control of signal processing.

As shown in FIG. 2, the insertion portion 102 includes the light guide 14 that introduces light emitted from the light source portion 41 to the distal end portion 103, a signal line to transmit an image of a subject obtained by the CCD 21 to the body processing device 43, a channel 28 that enables insertion of a treatment instrument for performing treatment, or the like. A treatment instrument insertion opening 29 for inserting a treatment instrument into the channel 28 is provided in the vicinity of the operation portion 104.

The body processing device 43 is, similarly to the light source portion 41, connected to the scope 101 via the connector 11. To the body processing device 43, the CCD drive circuit 45 for driving the CCD 21 is provided.

In response to application of a CCD drive signal from the CCD drive circuit 45, a signal photoelectrically converted in the CCD 21 is inputted into a sample/hold portion 46 that forms a signal processing system in the body processing device 43.

The sample/hold portion (hereinafter, referred to as S/H portion) 46 includes S/H circuits 46a to 46c that sample or hold RGB signals and output the signals, and S/H circuits 46d to 46f that sample or hold $\lambda 1$ to $\lambda 3$ signals and output the signals.

In the specification, for simplicity, signals captured in pixels that are provided with RGB filters are referred to as RGB signals, and similarly, signals captured in pixels that are provided with $\lambda 1$ to $\lambda 3$ filters are referred to as $\lambda 1$ to $\lambda 3$ signals.

In FIG. 2, for example, an example that the scope 101B is connected to the endoscope apparatus body 105 is illustrated. In such a case, as shown in FIG. 2, the S/H circuits 46d to 46f output the sampled or held $\lambda 1$ to $\lambda 3$ signals.

On the other hand, in a case where the scope 101 is connected to the endoscope apparatus body 105, among the S/H circuits 46d to 46f, only the S/H circuit 46d outputs the $\lambda 1$ signal.

In the S/H portions 46, operation to sample or hold is controlled by the control portion 42.

The outputted signals of the S/H portions 46 are inputted into a color signal processing portion 47, and separated into wideband RGB signals and narrowband $\lambda 1$ to $\lambda 3$ signals (or $\lambda 1$ signal).

In a case where the scope 101B is connected to the endoscope apparatus body 105, the color signal processing portion 47 outputs wideband RGB signals to a normal image generation portion 48 and outputs narrowband $\lambda 1$ to $\lambda 3$ signals to a narrowband image generation portion 49.

The normal image generation portion 48 performs processing to generate a normal image such as γ correction to the RGB signals, and outputs the RGB signals corresponding to the normal image to RGB channels of Rch, Gch, and Bch of the display monitor 106 through a composition/selection portion 50.

The narrowband image generation portion 49 performs processing such as γ correction, and color conversion to the narrowband $\lambda 1$ to $\lambda 3$ signals and generates narrowband image signals F1, F2, and F3 corresponding to a narrowband image. Then, the narrowband image generation portion 49 outputs the signals to the ROB channels of the Rch, Gch, and Bch of the display monitor 106 through the composition/selection portion 50.

The composition/selection portion 50 includes a function to compose or superimpose the RGB signals outputted from the normal image generation portion 48 and the $\lambda 1$ to $\lambda 3$ signals outputted from the narrowband image generation portion 49, and a function to select one of the both signals and outputs the selected signal.

Users (operators) can select the composite/selection function of the composite/selection portion 50. For example, in response to a user's operation of the composite or selection instruction through a scope switch 51 provided in the scope 101 or the scope 101B, the instruction signal is transmitted to the control portion 42. According to the instruction signal, the control portion 42 controls the function of composite/selection of the composite/selection portion 50.

Moreover, as shown in FIG. 2, for example, it is possible to display a narrowband image Ib adjacent to a normal image Ia, or display (a selected image) according to a user's switching operation.

Especially, in a case where the normal image and the narrowband image can be simultaneously displayed, it is very advantageous in diagnosis because the normal image and the narrowband image during a general observation can be readily compared with each other, and the observation can be performed in consideration with the respective characteristics.

More specifically, the characteristic of the normal image resides in that the color tone of the normal image is similar to that of ordinary observation by the naked eye, and the observation can be readily performed. The characteristic of the narrowband image resides in that the narrowband image enables observation of predetermined portions such as blood vessels which are not observed in the normal images.

The control portion 42 controls a color adjustment portion 49a provided in the narrowband image generation portion 49. The color adjustment portion 49a adjusts (determines) a color tone in color-displaying the narrowband image Ib on the display monitor 106.

The user can perform instruction operation through a color adjustment operation portion on an operation panel (not shown) provided in the scope switch 51 or the body processing device 43 to control color adjustment operation performed by the color adjustment portion 49a through the control portion 42. Further, it is possible to display the narrowband image Ib in a display color tone good in visibility on the display monitor 106.

In FIG. 2, in a case where the scope 101 is connected to the endoscope apparatus body 105, the color signal processing portion 47 outputs a G signal and a λ1 signal to the narrowband image generation portion 49.

Then, based on the two signals, the narrowband image generation portion 49 generates narrowband image signals F1, F2, and F3 to be outputted to the R, G, B channels Rch, Gch, and Bch in the display monitor 106.

The narrowband image generation portion 49, in a case where the inputted signals are the λ1 to λ3 signals, without performing the color adjustment, can generate the narrowband image signals F1, F2, and F3 to be allocated (outputted), for example, λ1→Bch, λ2→Och, and λ3→Rch.

Moreover, the narrowband image generation portion 49, in a case where the inputted signals are the G signal and a λ1 signal, outputs the narrowband image signals F2 and F3 allocated, for example, G→Gch, and λ1→Bch. In such a case, the F1 signal is not outputted. Alternatively, the narrowband image generation portion 49 may output the narrowband signals F2 and F3 that are allocated G→Gch, and λ1→Bch.

Moreover, it is possible to perform color adjustment corresponding to the user's preference by transmitting an instruction signal to the color adjustment portion 49a of the narrowband image generation portion 49 from the scope switch 51 or the like through the control portion 42.

In such a case, in the case where the inputted signals are the λ1 to λ3 signals, the color adjustment portion 49a can generate, for example, with coefficients k1 and k2, the narrowband signals F1, F2 and F3 that are allocated λ1→Bch, k1×λ1+k2×λ2→Gch, and λ3→Rch.

Moreover, by changing the values of the coefficients k1 and k2, color tones to be displayed can be changed. It is noted that color adjustment other than the above may be performed. Further, in the case where the inputted signals are the G signal and the λ1 signal, the colors may be adjusted, for example, k1×G+k2×λ1→Gch, and λ1→Bch.

Operation according to the configuration according to the present embodiment will be described.

A user such as an operator connects a scope to be used for endoscopy to the endoscope apparatus body 105. For example, in a case where the user wants to observe conditions of a surface of mucous membrane in detail, as shown in FIG. 3B, the scope 101B that is equipped with the CCD 21 provided with the color filter portion 22B is used.

In response to the connection of the scope 101B to the endoscope apparatus body 105, an ID of the ID portion 44 is read by the control portion 42, and the control portion 42 identifies that the scope connected to the endoscope apparatus body 105 is the scope that is equipped with the CCD 21 provided with the color filter portion 22B.

Then, the control portion 42 controls the S/H portion 46, and to the color signal processing portion 47, RGB signals and narrowband λ1 to λ3 signals are inputted from the S/H portion 46.

The color signal processing portion 47, the color signal processing portion 47, for example, internally amplifies the RGB signals and the narrowband signals λ1 to λ3 which are inputted, and outputs wideband ROB signals to the normal image generation portion 48 and narrowband signals λ1 to λ3 to the narrowband image generation portion 49 respectively.

The normal image generation portion 48, for example, performs A/D conversion of the inputted signals and temporarily stores the signals in a memory. Then, the normal image generation portion 48 simultaneously reads out the RGB signals, performs γ correction or the like, performs D/A conversion, and outputs the signals as RGB signals for normal image display to the display monitor 106 through the composite/selection portion 50. Then, on the display monitor 106, a normal image Ia is displayed.

On the other hand, the narrowband image generation portion 49 performs A/D conversion on inputted nanoband signals λ1 to λ3 and temporarily stores the signals in a memory. Then, the narrowband image generation portion 49 simultaneously reads out the stored signals λ1 to λ3, performs γ correction or the like, performs D/A conversion, and outputs the signals as signals of F1 to F3 for narrowband image display to the display monitor 106 through the composite/selection portion 50. Then, if the user has performed an instruction to select to display the narrowband image, on the display monitor 106, a narrowband image Ib is also displayed.

In such a case, by performing color adjustment by the color adjustment portion 49a, the narrowband images can be displayed in color tones good in visibility.

The user can, as shown in FIG. 2, simultaneously cause to display the normal image Ia and the narrowband image Ib on the display monitor 106. In such a case, the narrowband image Ib may be a moving image displayed in real time, and the image is generated based on a signal obtained by capturing light reflected from the observation subject such as mucous tissue in the body cavity through the narrowband filters λ1 to λ3. Accordingly, since the narrowband image is generated directly from the signal captured in the narrow band, not generated indirectly from the wideband signal by the signal processing (image processing) as in the case of the second known art, a highly reliable narrowband image can be generated.

Moreover, for the single-CCD 21, the filter formed by two-dimensionally arranging the RGB filters and the filters λ1 to λ3 is used. Accordingly, as compared with the fourth known art, it is ensured to have the narrower-diameter insertion portion 102, and the insertion use, that is, endoscopy can be performed in more portions. Further, as compared with the fourth known art, insertion operation can be more easily performed.

According to the present embodiment, even in a case where reflection characteristics of the observation subject varies, the normal image Ia and the narrowband image Ib can be simultaneously obtained. This is advantageous for observation or diagnosis of vascular networks in a surface layer in a body cavity.

The endoscopy may be performed using the scope 101 that employs the color filter portion 22 shown in FIG. 3A.

In such a case, obtainable narrowband image information is reduced since the number of the narrowband filters in different wavelength bands is smaller than that of the color filter portion 22B. However, the scope 101 has the λ1 filter whose wavelength is close to the shortest wavelength in the visible band, it is possible to obtain a narrowband image that clearly shows blood running conditions of a surface layer portion of a biological mucous membrane effective for screening of early cancer or the like.

In the case of the scope 101, only one filter is used for the narrowband λ1 filter. Accordingly, the unit pixel size is similar to those of existing normal image filters (that is, filters that have arranged RGB filters), and it is possible to narrow the diameter as compared with the scope 101B.

In the fourth known art, it is disclosed that blood information is calculated based on information respectively captured in wavelengths including wavelengths where light absorption degrees vary depending on variation of oxygen saturation degrees of hemoglobin and wavelengths where the light absorption degrees do not vary so much. On the other hand, in the present embodiment, there is the advantage that desired image information can be obtained using one narrowband wavelength.

As described above, according to the present embodiment, it is possible to provide the electronic endoscope that ensures the narrow diameter insertion portion and is suitable to obtain normal images and narrowband images.

Figure 6A:
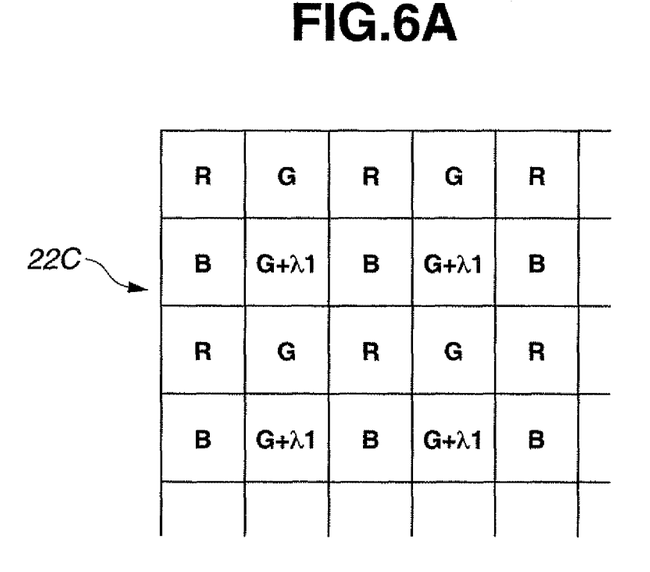
FIG. 6A is a view illustrating a filter array configuration of a color filter portion according to a first modification.

In place of the color filter portion 22 shown in FIG. 3A, a color filter portion 22C shown in FIG. 6A may be used. The color filter portion 22C employs, in the color filter portion 22 shown in FIG. 3A, in place of the λ1 filter, for example, a (G+λ1) filter (in FIG. 6A, expressed as G+λ1) that has transmission characteristics of the G filter and the λ1 filter is employed.

In the case where the color filter portion 22C is employed, to obtain a G signal and a λ1 signal from a signal captured using the (G+λ1) filter, between the S/H portion 46 and the color signal processing portion 47 in the body processing device 43 in FIG. 2, for example, a 1 H delay line is provided and processing is performed as follows.

At a timing the signal captured using the (G+λ1) filter is inputted into the S/H portion 46 in the body processing device 43, a S/H circuit 46*b* and a S/H circuit 46*d* are instructed to sample or hold the signal. The (G+λ1) signal sampled or held by the S/H circuit 46*b* is considered as a G signal and inputted in the color signal processing portion 47.

On the other hand, the G signal that is 1 H delayed in the 1 H delay line and sampled or held is subtracted from the (G+λ1) signal sampled or held in the S/H circuit 46*d* to generate a λ1 signal, and the λ1 signal is inputted in the color signal processing portion 47.

The above-described case has been described using the RGB filter of primary colors as the wideband filter, however, it is possible to use a complementary color filter.

Figure 6B:
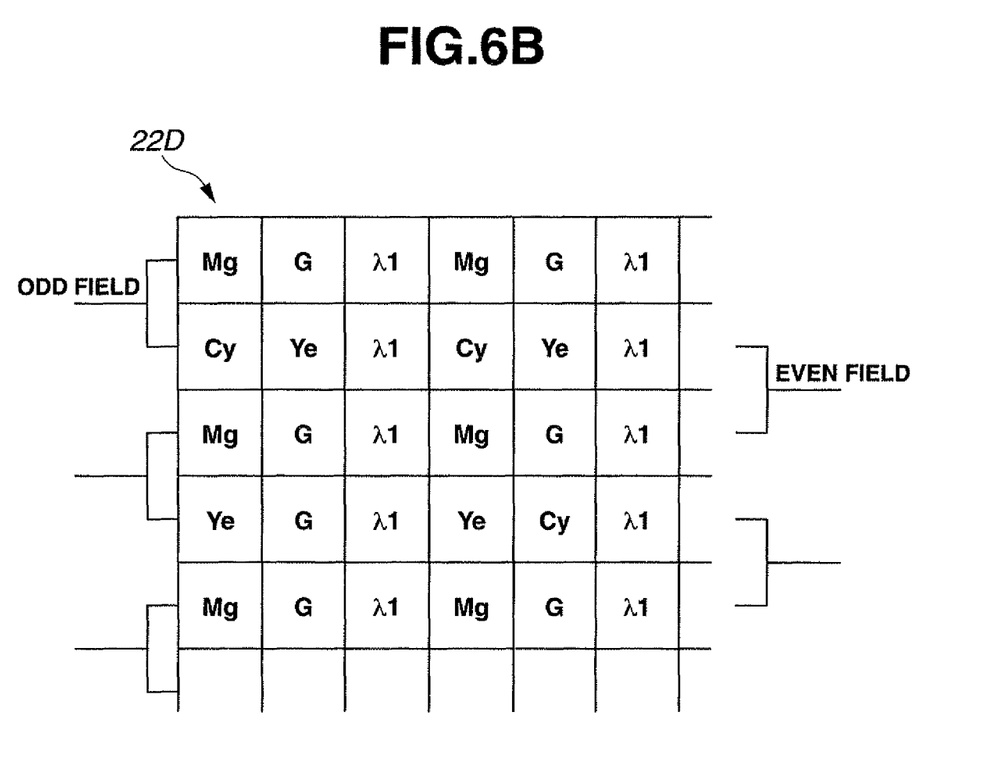
FIG. 6B is a view illustrating a filter array configuration of a color filter portion according to a second modification.

For example, FIG. 6B illustrates a color filter portion 22D formed by two-dimensionally arranging a λ1 filter together with Mg, G, Cy, and Ye filters of complementary colors. If the λ1 filter is not provided, the filter is similar to normal complementary filters. In the present case, as shown in FIG. 6B, pixels adjoining in a vertical direction in odd fields and even fields are added and read out.

In the case of FIG. 6B, by providing the λ1 filter, a narrowband image signal formed using the λ1 filter can be obtained.

Moreover, in FIG. 6B, the λ1 filter is added to the Mg, G, Cy, and Ye filters of complementary colors. However, a λ2 filter, a λ3 filer, or the like may be further provided. For example, to provide the λ2 filter, the λ2 filter line may be disposed between a column of the λ1 filters and a column of the filters of Mg, Cy, . . . .

In the present embodiment, wavelengths of the λ2 filter and the λ3 filer are not limited to those shown in FIG. 5. For example, a wavelength whose transmission band is set near a center of a green wavelength or a wavelength whose transmission band is set to longer-wave side may be used.

The body processing device 43 shown in FIG. 2 may be used in existing scopes that has the CCD 21 that is not provided with the narrowband λ1 filter but provided with the wideband RGB filters. In such a case, generation of narrowband images is not performed.

The body processing device 43 (as endoscope signal processing device) according to the present embodiment can correspond to the existing scopes that generate normal color images under illumination of white light (light in visible band), and can also correspond to the scope 101 and the scope 101B that have the solid-state image sensing devices that are provided with the narrowband filter. In such a case, as described above, normal images (color normal images) and narrowband images can be generated with the simple configuration.

(Second Embodiment)

Figure 7:
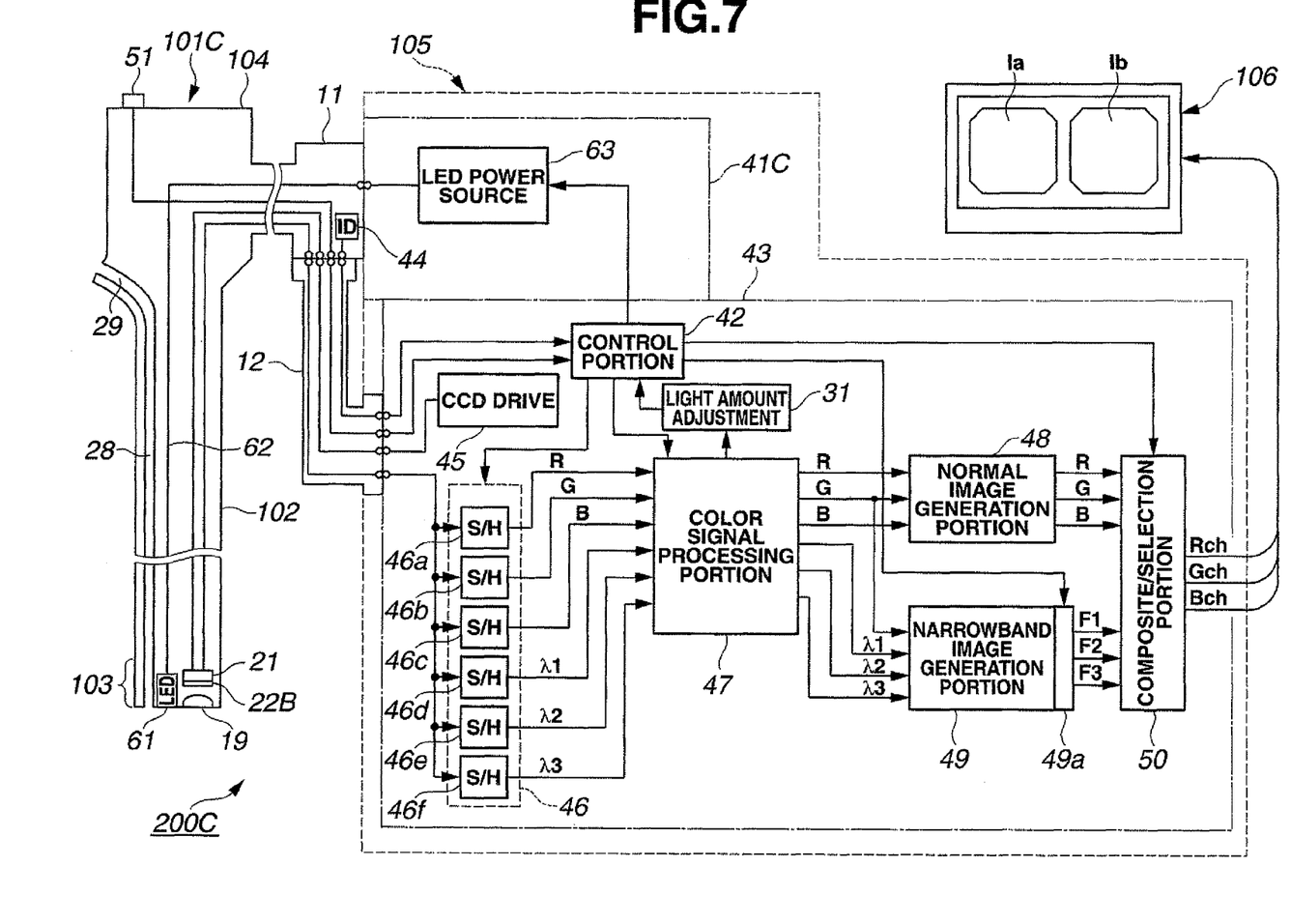
FIG. 7 is a block diagram illustrating a configuration of an electronic endoscope apparatus according to a second embodiment of the present invention.

FIG. 7 illustrates an electronic endoscope apparatus 200C according to a second embodiment of the present invention. The electronic endoscope apparatus 200C, in the electronic endoscope apparatus 200 in FIG. 2, employs a scope 101C that incorporates a light emitting element in place of the scope 101B, and employs a power source portion 41C to drive the light emitting element in place of the light source portion 41 in FIG. 2.

The scope 101C, in the scope 101B in FIG. 2, is provided with a white light emitting diode (briefly referred to as LED) 61 that emits white light in the distal end portion 103 without the light guide 14.

The white LED 61 is connected with an LED power circuit 63 in the power source portion 41C via a power source line 62 that is inserted through the insertion portion 102 or the like. The white LED 61 emits white light by supplying LED drive power from the LED power circuit 63. The white illumination light is outputted from an illumination window and illuminates an inspection target portion such as a living tissue surface in a subject or the like.

On an observation window adjacent to the illumination window, similarly to the case of FIG. 2, the objective optical system 19 is mounted. At the point where an image is formed, the CCD 21 having the color filter portion 22B is disposed.

The LED power circuit 63 is connected with the light amount control circuit 31 through the control portion 42. Based on the light amount control signal from the light amount control circuit 31, the LED power circuit 63 controls, for example, LED drive power to adjust a light emission amount to be illumination light to an appropriate value.

The other configurations are similar to those in FIG. 2. In the present embodiment, the power source line 62 is inserted through the insertion portion 102 in place of the light guide 14. Accordingly, it is possible to narrow the diameter of the insertion portion 102 more easily as compared with the scope 101B.

The other operation and advantages are similar to those in the first embodiment.

It is noted that in place of the white LED 61, three LEDs that emit light of three primary colors in a wide band of R, G, and B may be employed.

Embodiments obtained by partly combining each embodiment described above also constitute the present invention.

Industrial Applicability

In a visible band, by providing a single solid-state image sensing device provided with two-dimensionally arranged color filters having wideband transmission characteristics and a narrowband filter having a narrowband transmission characteristic to a distal end portion of an insertion portion, a narrower diameter insertion portion is realized. Further, under normal illumination light of visible band, wideband normal images and reliable narrowband images can be obtained. This enables to perform observation or diagnosis of vascular networks in a surface layer of biological mucous membrane more easily.

This application claims priority from Japanese Patent Application No. 2005-207509 filed on Jul. 15, 2005, and the contents disclosed above are hereby incorporated by reference herein in the specification of the present invention, claims, and drawings.

The invention claimed is:

1. An endoscope apparatus comprising:
   an endoscope including:
      an elongated insertion portion including a distal end portion provided with an illumination window and an observation window;
      an objective optical system mounted on the observation window;
      a single solid-state image sensing device having an image pickup face disposed at an image forming position of the objective optical system; and
      a filter portion disposed in the vicinity of the image pickup face of the solid-state image sensing device, the filter portion including:
         a first filter including three or more wideband filters each having a wideband wavelength transmission characteristic; and
         a second filter having a narrowband wavelength transmission characteristic in a visible band which is narrower than the wideband wavelength transmission characteristics of the wideband filters,
         wherein the at least three or more wideband filters are capable of separating colors into three primary colors under illumination of white light to cover the visible band, and the first filter and the second filter are arranged at an interval on a same two-dimensional plane; and
   signal processing means including:
      a normal image generation portion including a color signal extraction portion for extracting color signals picked up through the three or more wideband filters constituting the first filter with respect to an outputted signal of the solid-state image sensing device captured under the illumination of the white light, and generating a color normal image signal in the visible band from the color signals extracted by the color signal extraction portion;
      a narrowband image generation portion for generating a narrowband image signal in the visible band while selectively performing color adjustment based on a signal picked up through the second filter with respect to the outputted signal of the solid-state image sensing device captured under the illumination of the white light during a same illumination period as when the color normal image signal is generated; and
      an output selection portion for at least simultaneously outputting the color normal image signal generated by the normal image generation portion and the narrowband image signal generated by the narrowband image generation portion.

2. The endoscope apparatus according to claim 1, wherein the narrowband image generation portion comprises color tone adjustment means for a case of color-displaying the narrowband image signal by display means.

3. The endoscope apparatus according to claim 1, further comprising display means for displaying an image of the color normal image signal and an image of the narrowband image signal.

4. The endoscope apparatus according to claim 1, wherein the narrowband image generation portion generates the narrowband image signal in a moving state.

5. The endoscope apparatus according to claim 1, wherein the filter portion is formed in such a way that the first filter and the second filter are arranged on the same two-dimensional plane in a period of a filter array unit with which a color normal image and a narrowband image in the visible band are each simultaneously generated.

6. The endoscope apparatus according to claim 1, wherein the second filter's transmission wavelength is set within at least a blue wavelength band.

7. The endoscope apparatus according to claim 1, wherein the second filter comprises filters of a first transmission wavelength set within at least a blue wavelength band, and a second transmission wavelength set to a transmission wavelength different from that of the first transmission wavelength.

8. The endoscope apparatus according to claim 1, wherein the signal processing means further comprises a signal separating portion that separates one frame of the outputted signal of the solid-state image sensing device picked up under the illumination of the white light into the color signals picked up through the three or more wideband filters and a narrowband signal picked up through the second filter, and
   the signal separating portion outputs the color signals and the narrowband signal separated by the signal separating portion to the normal image generation portion and the narrowband image generation portion, respectively.

9. The endoscope apparatus according to claim 1, further comprising a white light generating light source for generating the white light, wherein
   the endoscope emits only the white light generated from the illumination window by the white light generating light source, as illumination light for when the solid-state image sensing device picks up an image.

10. The endoscope apparatus according to claim 1, wherein the normal image generation portion and the narrowband image generation portion simultaneously generate one frame of the color normal image signal and one frame of the narrowband image signal from one frame of outputted signal outputted from the solid-state image sensing device picked up under the illumination of the white light.

11. The endoscope apparatus according to claim 1, wherein the signal processing means comprises the output selection portion for performing selection from simultaneous output of the color normal image signal and the narrowband image signal and in addition output that selectively outputs only one of the image signals.

\* \* \* \* \*